(12) United States Patent
Reisinger

(10) Patent No.: US 6,981,618 B2
(45) Date of Patent: Jan. 3, 2006

(54) CONTAINER ASSEMBLY FOR A SUBSTANCE TO BE APPLIED

(75) Inventor: Michael Reisinger, Ruggell (LI)

(73) Assignee: Ivoclar Vivadent AG, Schaan (LI)

(*) Notice: Subject to any disclaimer, the term of this patent is extended or adjusted under 35 U.S.C. 154(b) by 86 days.

(21) Appl. No.: 10/266,709

(22) Filed: Oct. 8, 2002

(65) Prior Publication Data

US 2003/0075624 A1 Apr. 24, 2003

Related U.S. Application Data

(60) Provisional application No. 60/334,303, filed on Nov. 29, 2001.

(30) Foreign Application Priority Data

Oct. 18, 2001 (DE) .............................. P 101 51 404

(51) Int. Cl.
*A61C 5/04* (2006.01)

(52) U.S. Cl. ..................... 222/326; 222/386; 222/562; 433/90

(58) Field of Classification Search ................. 433/90; 222/23, 25, 386, 562, 325–327
See application file for complete search history.

(56) References Cited

U.S. PATENT DOCUMENTS

| | | | |
|---|---|---|---|
| 3,581,399 A | | 6/1971 | Dragan |
| 4,150,673 A | * | 4/1979 | Watt ............................ 222/80 |
| 4,472,141 A | | 9/1984 | Dragan |
| 4,519,518 A | | 5/1985 | Wiles et al. |
| 4,619,640 A | | 10/1986 | Potolsky et al. |
| 4,758,158 A | * | 7/1988 | Pierce et al. .................. 433/90 |
| 4,828,113 A | * | 5/1989 | Friedland et al. ........... 206/570 |
| 4,997,371 A | * | 3/1991 | Fischer ......................... 433/90 |
| 5,561,208 A | * | 10/1996 | Takahashi et al. .......... 526/281 |
| 5,662,472 A | * | 9/1997 | Grutzner ...................... 433/90 |
| 5,800,169 A | * | 9/1998 | Muhlbauer ................... 433/90 |
| 5,858,332 A | * | 1/1999 | Jensen et al. ................. 424/53 |
| 6,135,771 A | * | 10/2000 | Dragan et al. ................ 433/90 |
| 6,258,379 B1 | * | 7/2001 | Weinstein et al. .......... 424/451 |
| 6,780,012 B1 | * | 8/2004 | Peterson ....................... 433/90 |

FOREIGN PATENT DOCUMENTS

| | | |
|---|---|---|
| DE | 3927737 C2 | 1/1991 |
| DE | 3510747 C2 | 12/1993 |
| DE | 10061062 A1 | 8/2001 |
| EP | 0 063 891 A1 | 11/1982 |
| EP | 0919206 A2 | 6/1999 |
| WO | WO 89/12428 A1 | 12/1989 |

* cited by examiner

*Primary Examiner*—Eric Keasel
(74) *Attorney, Agent, or Firm*—John C. Thompson; Alan S. Korman

(57) ABSTRACT

A container assembly for a substance to be applied is provided that includes a injector housing, an application tip, and a closure cap. The application tip and the closure cap are alternatively removably securable to the outlet end of the injector housing in a substantially fluid tight disposition. A first indicia is associated with the injector housing and a second indicia is associated with each of the application tip and the closure cap. The second indicia has an identity correspondence with the first indicia such that the presence of both the first indicia on the injector housing and the second indicia on the respective one of the application tip and the closure cap secured to the outlet end of the injector housing confirms that only the appropriate application tip or the appropriate closure cap has been secured to the injector housing.

14 Claims, 4 Drawing Sheets

CONTAINER ASSEMBLY FOR A SUBSTANCE TO BE APPLIED

CROSS-REFERENCE TO RELATED APPLICATIONS

This application claims foreign priority benefits under 35 U.S.C. §119(a)–(d) from German patent application ser. no. P 101 51 404.2 filed Oct. 18, 2001. In addition, this application claims the benefit under 35 U.S.C. §119(e) of U.S. provisional patent application Ser. No. 60/334,303 filed Nov. 29, 2001.

TECHNICAL FIELD

The present invention relates to a container for a substance to be applied.

BACKGROUND OF THE INVENTION

Containers of this type, which can be configured as, for example, injectors, have long been known. In EP-A1-0 063 891, one approach to configuring such a container includes an application tip with a closure cap, whereby pasty material is provided in the application tip. A plunger ram pushes an injection plunger into an injector housing, whereby the corresponding geometrical configuration of the injector plunger is chosen such that only the smallest possible remaining amount of material remains in the injector housing following the application of the material.

In accordance with the above-noted patent application, a closure cap is provided which is color-coded. The application of the color-coding ensures that the application tip and the closure cap are recognized as being elements associated with one another, such that an inadvertent placement of a closure cap on the incorrect application tip is avoided.

The background relating to the use of such containers is that different masses or substances can be applied with correspondingly colored, differently configured application tips. The different pasty masses comprise, in their applications in the dental practice, special properties which can be adversely impacted by contamination. It is, however, important that the dentist or the dental technician can rely upon the fact that the property of the applied mass or substance is, in fact, as promised.

The applied mass is typically, on the other hand, a photo polymerizable mass. The customary storage of such masses in a closed and light impermeable cabinet permits the use of masses which have been maintained in a relatively long storage state without quality degradation. If, on the other hand, the identification of a mass is to be undertaken based upon the application tip which applies the mass, which has been removed, it is important that the application tips also are stored in the normal course of use in a light impermeable cabinet in view of the fact, for example, that a yellow application body exhibits a considerably larger light transmission capability than a dark blue injector housing. For this reason, in accordance with the above-noted patent application, a substantially thick walled housing is provided.

It is, indeed, possible to choose a two-layer configuration for the injector housing and to produce the inner layer from a light blocking material. This approach is, however, clearly more expensive and requires a higher production precision for conforming the layer thicknesses to one another, for securing the layers to one another, and for assuring the sealing integrity.

A disadvantage of the heretofore deployed systems lies in the fact that the injector components must be manufactured together with the application tip. To be sure, the injector components can be manufactured as throw away or disposable articles which are still, basically, substantially cost favorable. However, there exists the problem that the viscosities of the masses to be applied vary. In this connection, it would be desirable to provide a suitable flow resistance in the application tip which is selected as a function of the viscosity of the mass to be applied. The dentist or dental technician should be able, to the extent possible, to apply the same actuation force independent of the viscosity of the mass to be applied, thus leading to an ergonomically optimized operation and permitting a delicately sensitive dosing.

In connection with known or conventional injector components, a trade-off has been accepted that the actuation force will vary in correspondence with the properties of the mass to be applied, as otherwise the production of numerous different injector components with diameters selected as a function of the viscosity of the masses would be too labor intensive. In addition, it must also be taken into account that the viscosity of newly developed masses varies. In this regard, typically a compromise has been struck with respect to configuring the flow resistance during the application of the mass in that it has been decided to configure the injector to have an average flow resistance to the mass to be applied.

On the other hand, the demand for applied dental masses is increasing so that it can be expected that, in the future, the number of masses to be applied having differing viscosities will increase still further.

OBJECTS AND SUMMARY OF THE INVENTION

The present invention offers a solution to the challenge of providing a container for the application of a mass, in particular, a pasty mass in the dental practice, which is substantially clearly better suited for hand application uses while nonetheless permitting savings to be achieved during the production thereof.

In accordance with the present invention, it is provided that the housing is combinable as a standard product with different application tips, which themselves can be made as commercially available products. In connection with the configuration of a container in accordance with the present invention as an injector, commercially available systems having a so-called clip lock connection can be used and can be correspondingly manufactured in a cost favorable manner. In accordance with the present invention, these combinations of injectors and application tips can each be provided with a suitable marking which forecloses the risk of an incorrect combination of these components with one another.

It is to be understood that suitable and clearly legible markings can be used. If, for example, six different masses are to be held ready in three different viscosities, it is favorable to deploy three suitable symbols as markings such as, for example, a circle, a four-sided symbol, and a triangle. It is to be understood that, in lieu of such geometric symbols, other suitable desired markings can also be used such as symbols or the like having indicia. For example, the differing injector diameters can be symbolically represented by symbols in the form, for example, of circles having widely differing diameters.

A further possibility lies in presenting the outlet diameters in millimeters.

It is particularly advantageous that the light protected injectors and application tips which are so marked can be used in a standard configuration while the markings can be selected according to color and shape.

It is to be understood that, in lieu of the so-called clip lock connection, another suitable desirable connection can be provided for interconnecting the injector housing and the application tip without departing from the scope of the present invention. Thus, for example, a bayonet connection can be deployed, whereby it is advantageous to use, in a conventional manner, an annularly-shaped seal which seals against the injector housing and the application tip.

It is further particularly advantageous that the markings can, by suitable application thereof, at the same time provide an optical feedback coupling which indicates the correct rotational position. Preferably, the markings are applied such that they align one over the other in conjunction with the secure interconnection of the clip lock connection components or the bayonet connection components.

In a preferred embodiment of the present invention, the volume of the injector is, in comparison to the volume of the application tip, substantially much greater. The volume difference can be, for example, 20:1 or even 100:1. The injector receives the mass in the manner of a storage container while the application tip or channel is configured as a throw away or disposable component.

In this embodiment, it is provided that a closure cap can be deployed on the injector housing. Such closure caps are in any event commercially available for the clip lock system. Preferably, in accordance with the present invention, the closure cap can itself be provided with a corresponding marking in order to reliably preclude the risk that contamination can occur by the placement in error of the closure cap on the non-associated one of a pair of injectors.

Also, if non-removable labels are disposed on the containers by, for example, pressing, imprinting, wear-resistant coloring, or the like, it is to be understood that it is also basically possible to implement the marking arrangement by means of such non-removable labels. Such labels offer the possibility to combine the markings with bar coding in order to improve the machine readability and, thereby, improve the atomization of the storage process.

BRIEF DESCRIPTION OF THE DRAWINGS

Further advantages, details, and features are provided herein below in connection with the description of a preferred embodiment of the present invention taken in connection with the figures of the drawing, in which.

DETAILED DESCRIPTION

Figure 1:
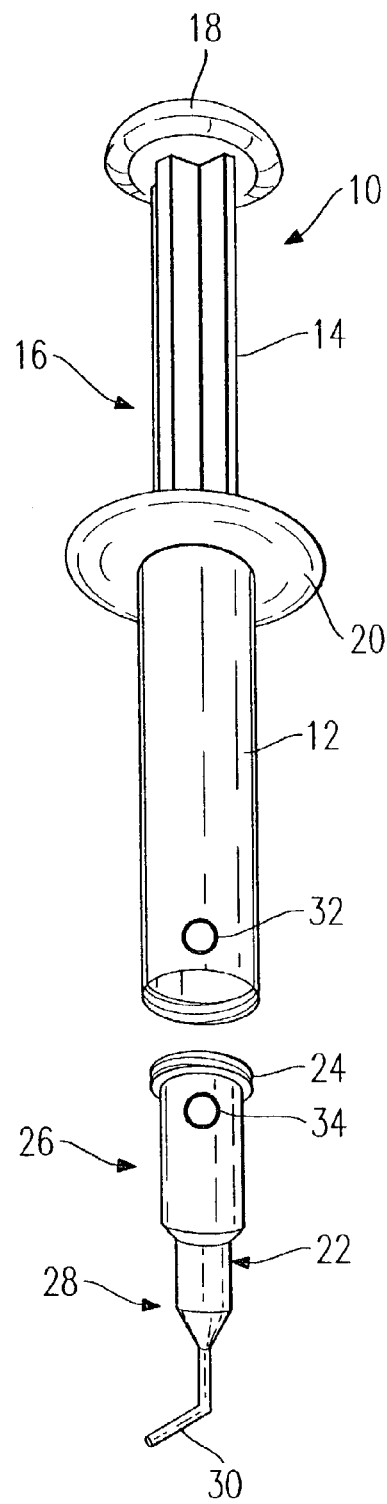
FIG. 1 is a front perspective view of an injector of an embodiment of the present invention having a first marking.

As shown in FIG. 1, an injector 10 includes an injector housing 12 which guides therein an injector plunger 14. With respect to the injector plunger 14 shown in FIGS. 1–3, only the shaft thereof is visible. To produce the required pressure, the shaft 16 includes a knob 18 on its outward end. In this connection, the injector housing 12 comprises a grip flange 20. A substantially large injection pressure can be applied by pressing together the knob 18 and the grip flange 20 between the palm of the hand and, for example, the middle and index finger, whereby the thus-applied pressure effects the forward movement or injection of the pasty mass contained in the injector housing 12.

An application tip 22 is connected to the forward portion of the injector housing 12. In this connection, the injector housing 12 comprises a substantially curved inner thread course at its forward end having a correspondingly large pitch. An outer thread course 24 on the rearward end of the application tip 22 conforms to the inner thread course of the injector housing. The conformation of the inner and outer thread courses to one another is accomplished such that there is very little free play therebetween.

The application tip comprises a cylindrical portion 26, a conical portion 28, and a truncated channel or tubular member 30.

It is also possible, if the volume of the application tip 22 is only relatively slightly smaller, by a single order of magnitude, than the volume of the injector housing 12, to nonetheless provide, in actual configurations of the application tip, an application tip which is smaller by substantially more than a single order of magnitude.

In accordance with the present invention, the injector housing 12 and the application tip 22 are provided with a marking 32, 34, respectively. Both markings correspond identically with one another and come into alignment with one another upon the firm interconnection of the application tip 22 with the injector housing 12.

In the illustrated embodiments, both markings are configured as circles.

Figure 2:
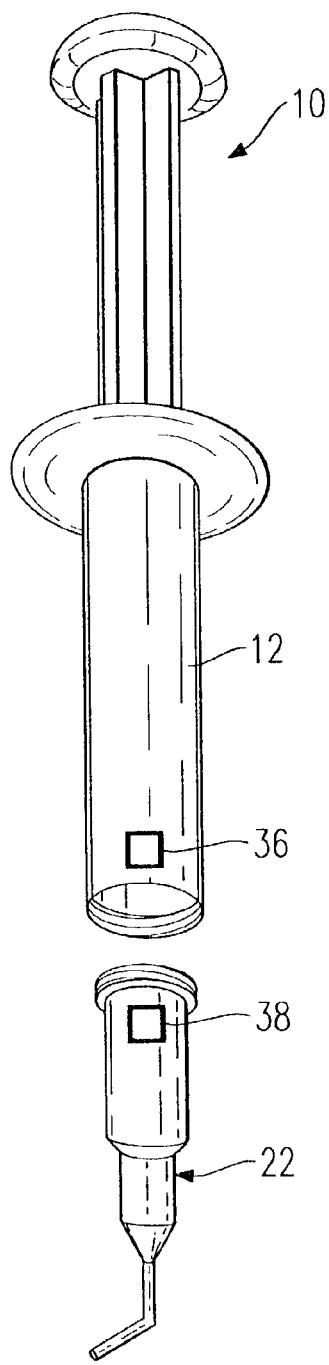
FIG. 2 is a front perspective view of an injector of an embodiment of the present invention having a second marking.

In accordance with the present invention, it is provided that a different marking is chosen with respect to another different mass to be applied. Thus, for example, FIG. 2 illustrates an injector 10 which otherwise corresponds with the injector 10 shown in FIG. 1, but comprises, instead, a marking 36 on the injector housing and a marking 38 on the application tip 22, these markings clearly being different than the markings 32 and 34 provided, respectively, on the injector housing 12 and the application tip 22 of the embodiment of the injector 10 shown in FIG. 1.

Figure 3:
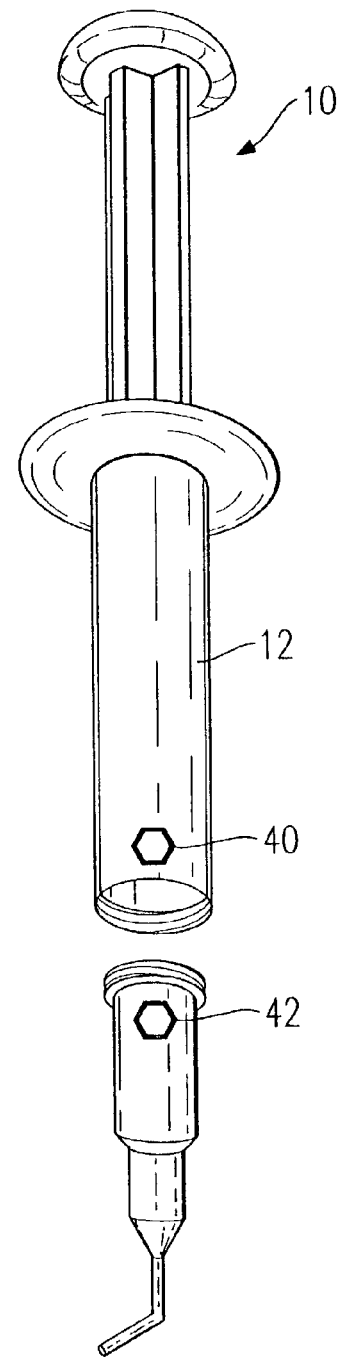
FIG. 3 is a front perspective view of an injector of an embodiment of the present invention having a third marking.

Likewise, another embodiment of the injector 10 of the present invention, shown in FIG. 3, otherwise corresponds with the injector 10 shown in FIG. 1, but comprises, instead, markings 40 and 42 which are configured as six-sided markings.

The markings can be applied in any desired suitable manner. In the illustrated embodiments of the injector 10 of the present invention, the markings are provided as corresponding punched out plastic components which are secured in a non-removable manner to the injector housing 12 or, respectively, the application tip 22.

Figure 4:
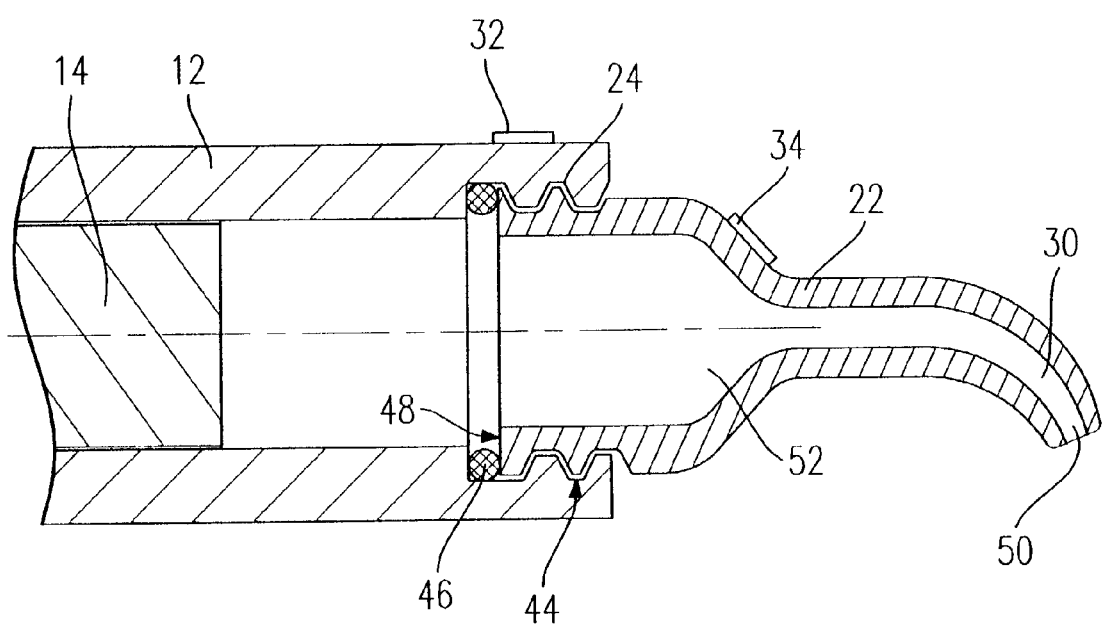
FIG. 4 is an enlarged sectional view of a front portion of an injector of the present invention.

FIG. 4 shows a preferred configuration of the interconnection between the injector housing 12 and the application tip 22. An inner thread course 44 threadably receives therein an outer thread course 24 of the application tip 22. A seal ring 46 extends between the back surface 48 of the application tip 22 and an inner corner of the injector housing 12.

The channel 30 of the application tip 22 has an inner diameter 50 which is precisely dimensioned to a selected value and which has a different value for each differently marked application tip. In connection with the application of a relatively high viscosity mass 52, which is received in the injector housing 12 for injection through the application tip 22, a relatively large inner diameter 50 is selected, while a relatively smaller diameter is selected for masses which are relatively less viscous. In this manner, the application force which must be applied for the injector plunger 14 to expunge the mass from the injector 10 is substantially the same for masses of varying viscosity, independent of the viscosity of the respective mass being applied.

The application tip 22 is thrown away or disposed of after use and a closure cap is threaded onto the injector housing 12 following the removal therefrom of the application tip 22. The closure cap is not illustrated but includes an outer thread course adapted to be threadably received by the inner thread course 44. The placement of the closure cap on the injector housing 12 permits long term storage of the mass retained in the injector housing without hardening of the mass.

Both the injector housing 12 and the application tip 22 are comprised of a black colored plastic such as, for example, a polyamide, and each is formed as an integral single piece unit.

Figure 5:
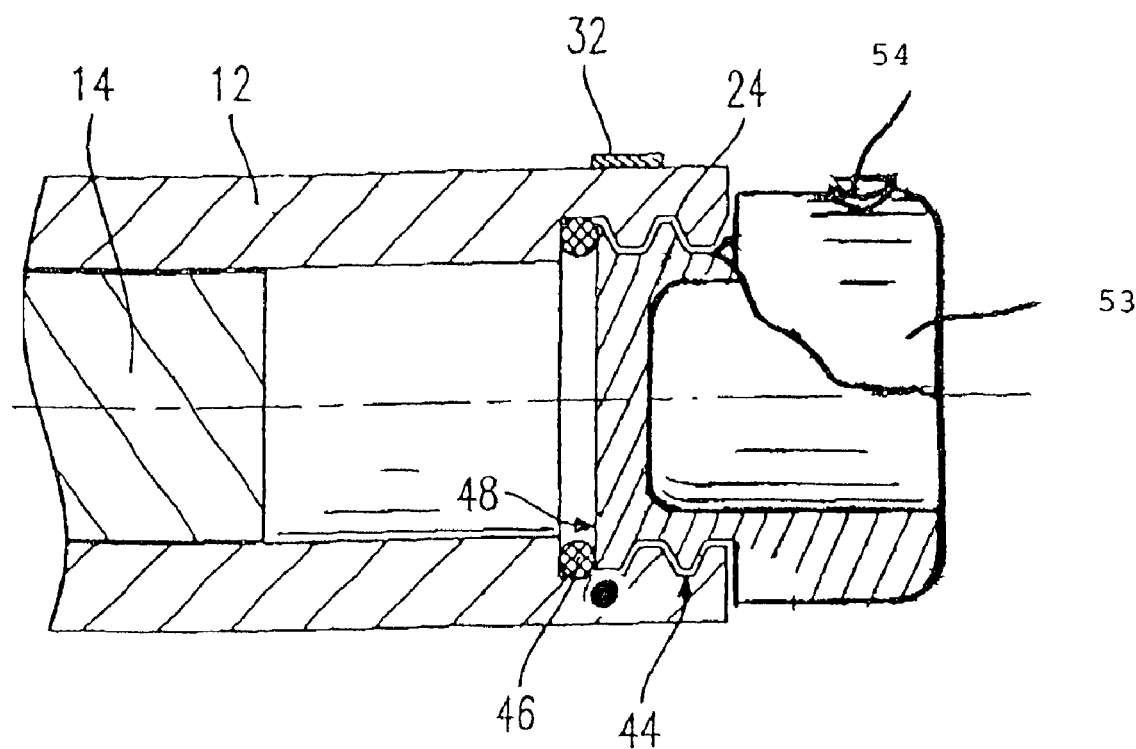
FIG. 5 is a diagrammatic view of a front portion of the present injector, partially broken away and sectioned.

FIG. 5 shows the front portion of an injector according to the present invention that can be used for storing purposes. The front portion of the injector is provided with a closing plug 53 which is screwed in instead of the application tip 22, serving as a closure cap. Accordingly, the closing plug 53 comprises an outer thread which also is adapted to be threadably received by the inner thread 44 of the injector housing 12.

The closing plug 53 also comprises a marking 54 which corresponds to the marking 32 and symbolizes the association to the corresponding injector.

Figure 6:
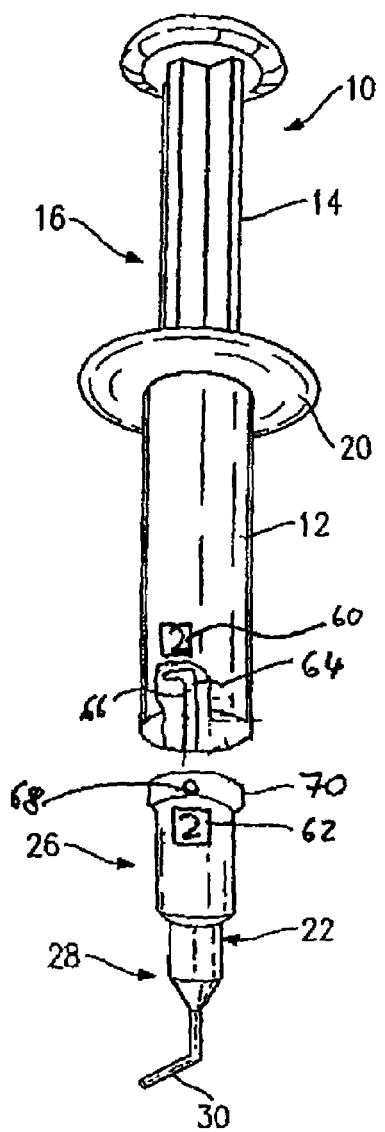
FIG. 6 shows another enibodiment with a bayonet locking assembly.

FIG. 6 shows another embodiment of the present invention. In this embodiment, instead of markings, numbers 60 and 62 are used. As an example, the number "2" is shown in FIG. 6 for an injector housing and an application tip which are assigned to each other. Of course, other suitable numbers may be used.

FIG. 6 also shows a single position locking assembly formed as a bayonet locking assembly. The bayonet locking assembly 64 is shown in a portion of the housing 12 partially broken away. It mainly consists of a groove 66 formed in the inner wall of the housing 12 which is suitable to receive a projection 68 formed on the outer diameter of the upper portion 70 of the application tip 22.

Figure 7:
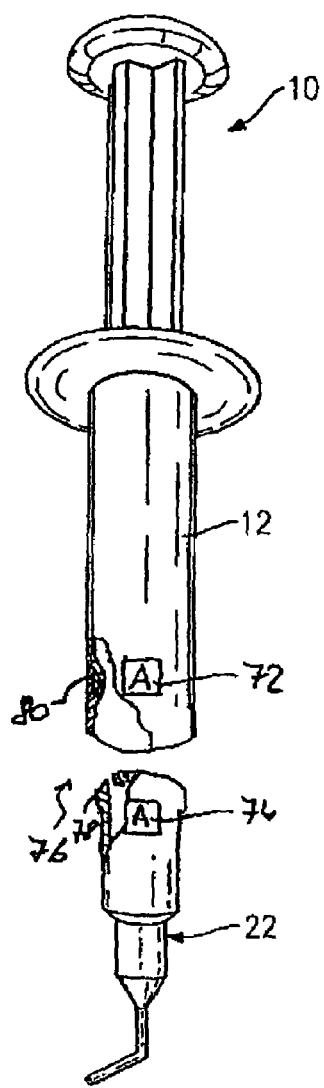
FIG. 7 shows a further embodiment with a clip lock assembly.

Another embodiment is shown in FIG. 7. With this embodiment, instead of numbers, letters 72 and 74 are used on the housing 12 and the application tip 22. In the example of FIG. 7, the letter "A" is used.

FIG. 7 also shows a single position locking assembly formed as a clip locking assembly 76. This embodiment has a resilient tongue 78 on the application tip 22 which is formed in a suitable manner to lock against a projection 80 formed on the inner wall of housing 12. The respective portion is shown broken away in FIG. 7.

Figure 8:
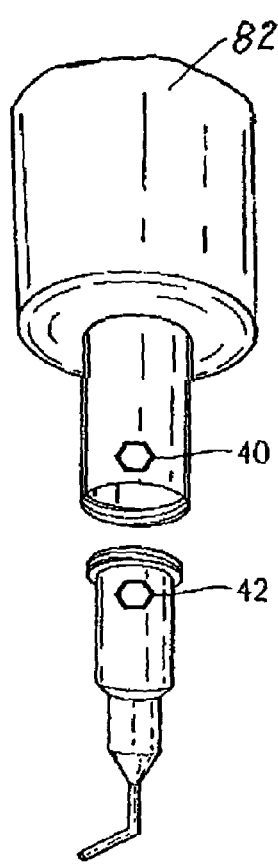
FIG. 8 shows a further embodiment with a bottle as the injector housing.

FIG. 8 is similar to FIG. 3, but shows a bottle 82 as the housing.

Simultaneously, matching of the horizontal turning position, i.e. alignment of the markings 32 and 54, ensures that the closing plug 53 is fixedly screwed in n the one hand, but on the other hand the inner thread is not overturned by the closing plug. Thus, finally also the pressing force exerted against the sealing 46 can precisely be set such that an optimum sealing is warranted. Accordingly, the screw threaded device illustrated can be considered a single position locking element in that only a single locking position is provided when the indicia 32 and 54 are aligned. While a screw connection has been illustrated, it should be obvious that other forms of connections may be utilized such as clip lock connection components or the bayonet connection components.

In summary, at least three differing injectors may be provided, each of which contains a differing material to be dispensed. Closure tips are also provided on each of the injectors, the closure tips being removed when the injector is to be used. The injectors and closure tips are identical, differing only in that different symbols are employed to indicate differing materials. When it is desired to dispense a material, the closure tip is removed and an application tip, which is designed for the specific material is connected to the injector. In the illustrated design, markings are provided on both the tip and the injector which will assure proper tightening of the tip into the injector. After use, the application tip is thrown away, but the injector is resealed by the closure cap which was previously removed. Differing application tips may have differing injector diameters.

The container of the present invention is not limited to an injector configuration. Instead, the container can alternatively be configured in an advantageous manner as a tube adapted to receive therein a pasty mass. Moreover, a container configured as, for example, a vial, can receive therein a mass in the form of a fluid or a powder.

The present invention is, of course, in no way restricted to the specific disclosure of the specification and drawings, but also encompasses any modifications within the scope of the appended claims. In addition, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A container assembly for a substance to be applied, comprising:
   an injector housing for retaining therein the substance to be applied, the housing having an outlet end through which the substance can exit the housing, and a first indicia associated with the injector housing;
   an application tip provided with means for removably securing the tip to the outlet end of the injector housing in a substantially fluid tight disposition such that, in the event that the application tip is secured to the outlet end, the substance retained in the housing can be dispensed from the housing through the application tip;
   a closure cap provided with means for removably securing the closure cap to the outlet end of the injector housing in a substantially fluid tight disposition such that, in the event that the closure cap is secured to the outlet end, the substance retained in the housing cannot exit the housing through the outlet end; a first indicia associated with the housing; and a second indicia associated with each of the application tip and the closure cap and having an identity correspondence with the first indicia such that the presence of both the first indicia on the housing and the second indicia on the respective one of the application tip and the closure cap secured to the outlet end of the housing confirms that only the preferred respective one of the application tip and the closure cap having the respective desired characteristic has been secured to the housing;

wherein the means for removably securing further comprises a single position locking assembly for removably securing each of the application tip and the closure cap to the injector housing, the single position locking assembly permitting rotational movement between the housing and the respective one of the application tip, and the closure cap being secured therewith between a release position and a lock position in which a locking element locks the respective one of the application tip and the closure cap into substantial fluid tight securement with the housing upon reaching a predetermined relative rotational position between the housing and the respective one of the application tip and the closure cap, wherein the first and second indicia are disposed on, respectively, the housing and the respective one of the application tip and the closure cap such that the first and second indicia are aligned with one another in the lock position to thereby visually indicate that the housing and the respective one of the application tip and the closure cap are in the lock position.

2. A container assembly for a substance to be applied according to claim 1, wherein the single position locking assembly is a bayonet locking assembly.

3. A container assembly for a substance to be applied according to claim 1, wherein the single position locking assembly further comprises a clip lock assembly for removably securing each of the application tip and the closure cap to the housing.

4. A container assembly for a substance to be applied according to claim 1, wherein the first and second indicia are configured as symbols.

5. A container assembly for a substance to be applied according to claim 1, wherein the first and second indicia are each configured as a selected one of numbers, letters, and a combination of numbers and letters.

6. A container assembly for a substance to be applied according to claim 1, wherein the second indicia on the application tip indicates in millimeters the cross sectional area of the tip exit.

7. A container assembly for a substance to be applied according to claim 1, wherein the application tip is configured as a disposable component and the closure cap is configured to close the outlet end of the housing upon removal of the application tip from the housing.

8. A container assembly for a substance to be applied according to claim 1, wherein the injector housing is configured as a mass producible item having a clip lock securing element on which the first indicia is disposed.

9. A container assembly for a substance to be applied according to claim 1, wherein the container substantially blocks the transmission of light therethrough and the housing has, in particular, a black color.

10. A container assembly for a substance to be applied according to claim 1, wherein the injector housing includes a cylinder and a plunger movable within the cylinder, the cylinder receiving therein the substance to be applied, and the plunger, upon the application of pressure, operating to expel the substance to be applied from the cylinder.

11. A container assembly for a substance to be applied according to claim 1, wherein the injector housing is a bottle.

12. A container assembly for a substance to be applied according to claim 1, wherein the injector housing is a tube.

13. A container assembly for a substance to be applied according to claim 1, wherein the substance to be applied is a powder.

14. A container assembly for a substance to be applied according to claim 1, wherein the substance to be applied is a fluid.

* * * * *